United States Patent [19]

Mima et al.

[11] 4,171,481
[45] Oct. 16, 1979

[54] APPARATUS FOR INSPECTING BOTTLES HAVING ELLIPTIC LIGHT CONVERGING MEANS

[75] Inventors: Yoshitada Mima, Tachikawa; Youji Kanno, Koganei; Nobuo Sato; Yasuhiko Hara, both of Yokohama; Yosiaki Tomita, Kodaira; Takuro Karakawa, Tokyo; Masahiro Miyamoto, Urawa; Toshitaka Kano, Tokyo, all of Japan

[73] Assignees: Hitachi, Ltd.; Sapporo Breweries Ltd.; Hitachi Denshi Kabushiki Kaisha, all of Japan

[21] Appl. No.: 887,965

[22] Filed: Mar. 20, 1978

[51] Int. Cl.$^2$ ............................................. G01N 21/32
[52] U.S. Cl. ................................ 250/223 B; 356/240
[58] Field of Search .................... 250/223 B, 228, 562, 250/563, 572; 356/239, 240

[56] References Cited

U.S. PATENT DOCUMENTS 3,834,822  9/1974  Stapleton et al. .................... 250/563

FOREIGN PATENT DOCUMENTS 2001019  7/1971  Fed. Rep. of Germany ........... 250/228

*Primary Examiner*—David C. Nelms
*Assistant Examiner*—Edward P. Westin
*Attorney, Agent, or Firm*—Craig and Antonelli

[57] ABSTRACT

An apparatus of the invention for inspecting bottles for detecting flaws or contamination in the bottles relies upon the light converging function performed by one open-sided elliptic cylinder having reflective inner surface and two foci. The point or line to be inspected of the bottle is positioned at one of the two foci, while at least one light receiving element is disposed at the other focus. A beam of light is applied to the point or line to be inspected of the bottle, so that, if there is any defect such as flaw or contamination, the light is reflected irregularly by the bottle in indefinite direction. The irregularly reflected fractions of light are reflected by the inner surface of the elliptic cylinder and converge on the light receiving element disposed at the other focus, so as to be effectively received by the same element. the presence of the defect, if any, is detected from the output of the light receiving element. Another light receiving element may be disposed outside of the elliptic cylinder so as to receive the fraction of light passed through the bottle.

23 Claims, 5 Drawing Figures

APPARATUS FOR INSPECTING BOTTLES HAVING ELLIPTIC LIGHT CONVERGING MEANS

BACKGROUND OF THE INVENTION

Field of the Invention

The present invention relates to an apparatus for examining or inspecting bottles for finding out defects such as flaw, contamination or the like, if any, through applying a light from a light source and receiving the light reflected by the bottles irregularly due to the presence of the defects.

Conventionally, there has been proposed and used photoelectric bottle inspecting apparatus having lighting means adapted to apply light to bottles to be inspected, and a group of light receiving elements, so as to detect the defects in the bottle, if any, through irregularity of reflected light.

This conventional technique, however, has suffered from disadvantage of difficulty in optimumly positioning the light receiving elements in relation with the random direction of irregularly reflected light, as well as difficulty in receiving all part of reflected light, which hinders the apparatus of this kind from being put into practical use.

According to another conventional technique, the defects are detected by photoelectric light receiving element or elements responsive to the reduction of quantity of light passing through the bottle due to the presence of defects.

This technique is also unsatisfactory especially for such effect as would not produce a sufficiently large contrast of the light having passed through the defective part to that having passed through the sound part of the bottle, e.g. kink, shell-shaped flaw, voids and so on, although it may be effectively used in detecting such defects as would hardly pass the light, e.g. inclusion of stones or other foreign matters and contamination.

SUMMARY OF THE INVENTION

It is therefore an object of the invention to provide a bottle inspecting apparatus which can overcome above described problems of the prior art.

More specifically, it is an object of the invention to provide a bottle inspecting apparatus in which the light scattered in random or indefinite directions by the defects such as flaws and contaminations of the bottle is suitably focussed to afford a more effective detection of the defects.

To this end, according to the invention, there is provided a bottle inspecting apparatus in which the point or line to be inspected of the bottle is positioned at one of two foci of an open-sided elliptic cylinder or sleeve, while a light receiving element is disposed at the other focus, so that the light reflected and scattered from the point or line to be inspected may be reflected by the inner surface of the elliptic cylinder and effectively converge on the light receiving element disposed at the other focus, so as to afford a more effective detection of defects than conventional apparatus.

These and other objects, as well as advantageous features of the invention will become more clear from the following description of the preferred embodiment taken in conjunction with the accompanying drawings.

BRIEF DESCRIPTION OF THE DRAWINGS

FIGS. 1, 3 and 5 in combination show the general arrangement of a bottle inspecting apparatus embodying the present invention, while

DESCRIPTION OF THE PREFERRED EMBODIMENT

Figure 1:
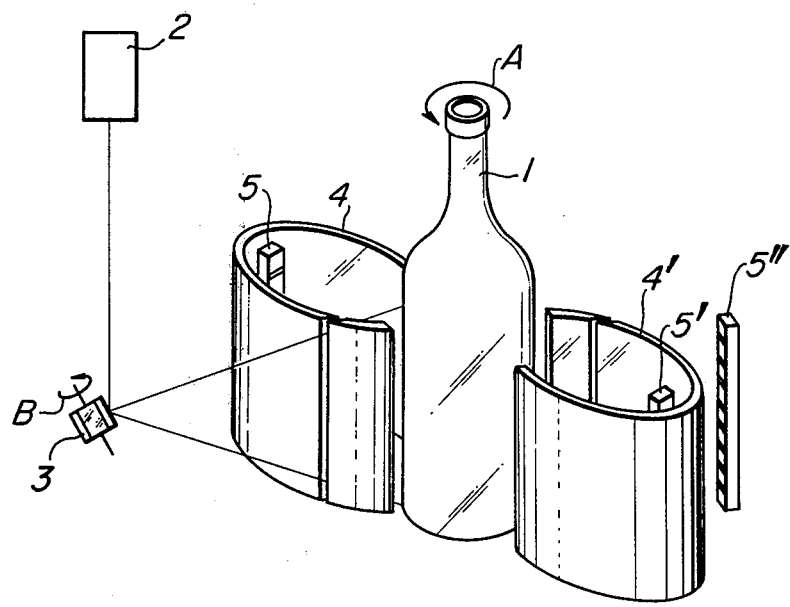

Referring first to FIG. 1 showing the general arrangement of an apparatus for inspecting empty bottles embodying the present invention, a bottle 1 to be inspecting is adapted to be rotated in the direction of arrow A. Reference numerals 2, 3, 4 and 4' denote a light source which may be a laser oscillator, multi-surface columnar rotary mirror and elliptic cylinders having reflective inner surfaces. The elliptic cylinder is adapted to allow the light emitted from the light source 2 to pass therethrough. Groups 5, 5', 5" of photoelectric conversion elements arrayed in the form of rods or bars are connected at their output sides to amplifiers (not shown).

The groups 5, 5' of photoelectric conversion elements are positioned at one of the foci of the elliptic cylinder. The bottle is scanned by the light reflected by the multi-surface columnar rotary mirror 3 which is rotated in the direction of arrow B, linearly through the slit formed in the elliptic cylinder.

Figure 2:
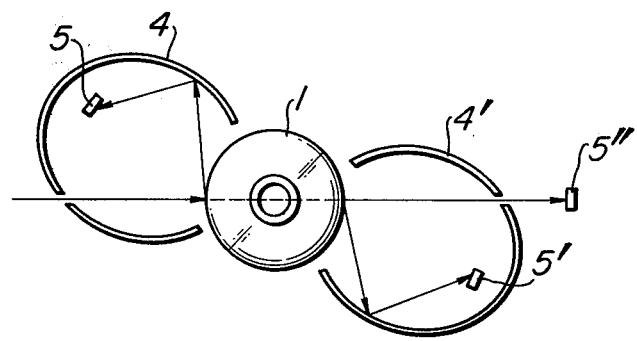
FIGS. 2 and 4 are plan views of the bottle inspecting apparatus.

Referring now to FIG. 2 which is a plan view illustrating the way of scanning, the light reflected from the multi-surface columnar mirror runs along paths as illustrated and finally received by the groups 5, 5', 5" of photoelectric conversion light receiving elements. It will be seen from FIG. 2 that the incident point at which the light comes into the bottle coincides with one of the foci of the elliptic cylinder 4, while the light having passed through the bottle leaves the same at a point located on one of the foci of the elliptic cylinder 4' so as to be directly received by the group 5" of the photoelectric conversion light receiving elements.

Provided that there is no defect such as flaw and contamination in the bottle, the whole part of the light reflected from the multi-surface columnar rotary mirror 3 runs straight through the bottle, so as to be directly received by the group 5" of the photoelectric conversion light receiving element, and no fraction of light is received by other groups 5, 5'.

However, if there is any defect such as flaw or contamination in the bottle, the light is scattered at the foci of the elliptic cylinders 4, 4', so that fractions of the light are received by the groups 5 or 5' of the photoelectric conversion light receiving elements. It will be seen that the presence of the defect can be detected by suitably comparing the electric outputs from the groups 5, 5', 5" of photoelectric conversion light receiving elements with one another.

As has been stated, there have been no effective measures to focus the random or irregularly reflected light on a point, although it has been noticed that the random or irregularly reflected light can be made use of in the bottle inspection, as an effective index of the presence of the defects in the bottle. However, according to the invention, the light scattered in all directions by the defects in the bottle can conveniently be converged on the light receiving element, by properly arranging the point to be inspected on one focus of the elliptic cylinder and the light receiving element at the other focus.

Figure 3:
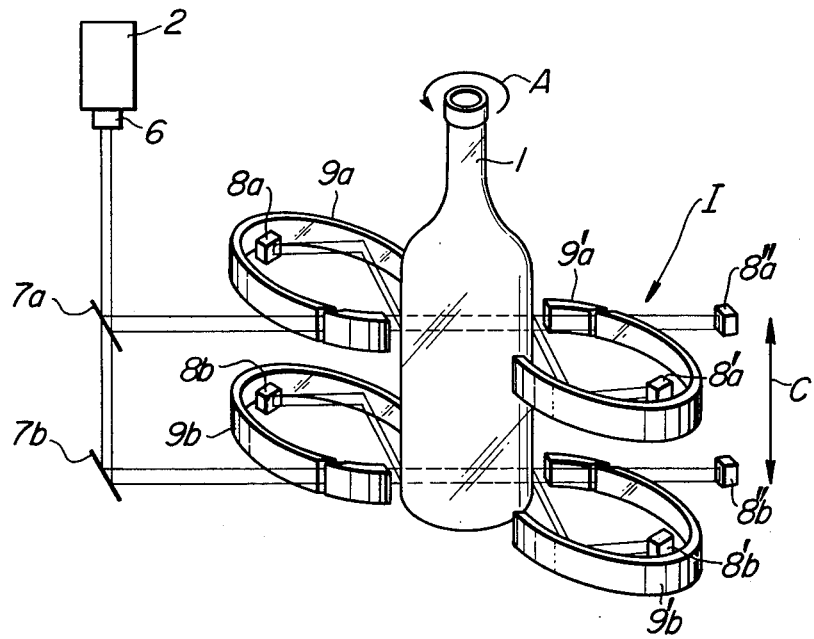
Figure 4:
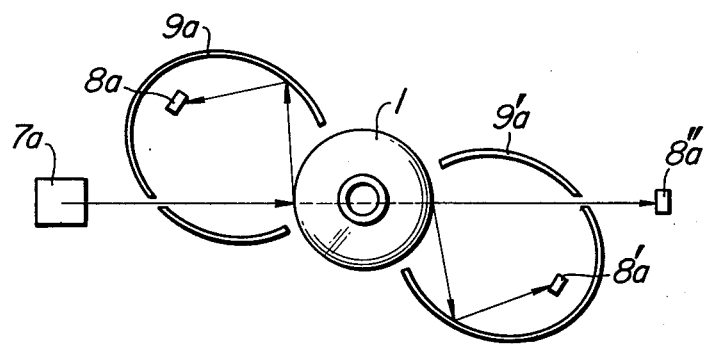

FIGS. 3 and 4 show the general arrangement and plan view of an automatic bottle inspection apparatus in accordance with another embodiment of the invention. In FIGS. 3 and 4, numerals 7a denotes a half mirror, while numeral 7b denotes a mirror. Photoelectric conversion light receiving elements are designated at numerals 8a, 8a', 8a'',8b, 8b', and 8b''. Numerals 9a, 9a', 9b and 9b' designate elliptic cylinders each of which having a reflective inner peripheral surface and a slit. These light receiving elements and elliptic cylinders in combination constitute one block I. Reference numerals 1 and 2 denote the same members as those in FIG. 1. Numeral 6 denotes a collimater.

The positional relationship of the empty bottle, elliptic cylinders and the photoelectric conversion light receiving elements as viewed in plan is identical to that of the embodiment as shown in FIGS. 1 and 2. In operation, the light emitted from the light source 2 such as a laser oscillator is changed to a flattened beam by the collimater 6, and is applied to the empty bottle 1, through the half mirror 7a and the mirror 7b, via the slits of the elliptic cylinders 9a and 9b. Meanwhile, the empty bottle 1 is rotated in the direction of arrow A, and the block I as a whole is moved in the vertical direction as shown by arrow C, so that the surface of the bottle 1 is throughly scanned by the light beam in a spiral manner.

The half mirror 7a, elliptic cylinders 9a, 9a' and light receiving elements 8a, 8a', 8a'' may be eliminated. However, in such a case, it is necessary to make the moving length of the block I longer than that of said embodiment.

Alternatively, the arrangement may be such that the bottle 1 is moved in the vertical direction as shown by arrow C and simultaneously rotated as shown by arrow A, while the block I is kept stationary.

It is still possible to vertically move and rotate the block I together with the laser light source as arrows A and C, while keeping the empty bottle stationary.

However, from the practical point of view, the first-mentioned spiral scanning is most preferred, because it is most easy to perform.

In this second embodiment, the detection of the flaw and contamination is made in the similar manner as the foregoing first embodiment.

More specifically, provided that there is no defect such as flaw and contamination in the bottle, the light reflected by the half mirror 7a (or mirror 7b) is directly received by the photoelectric conversion light receiving elements 8a''', (or 8b''), through the empty bottle 1. However, if there is any defects such as flaw or contamination in the bottle 1, the light beam is irregularly reflected at a focus of the elliptic cylinder 9a or 9a' (9b or 9b') and received by the photoelectric conversion light receiving elements 8a or 8a' (8b or 8b'). The resulting signal is suitably amplified and delivered outside as an output from the bottle inspection apparatus.

This embodiment is more advantageous than the foregoing embodiment in that it does not necessitate the rather expensive multi-surface columnar rotary mirror, which is indispensable in the foregoing embodiment, can be eliminated, and in that it does not require a large number of photoelectric conversion light receiving elements, so as to avoid disadvantages such as fluctuation of characteristic and small speed of response which are inherent in the rod-shaped group of elements, thereby to ensure a further enhanced precision in detecting the defects in the bottle.

Figure 5:
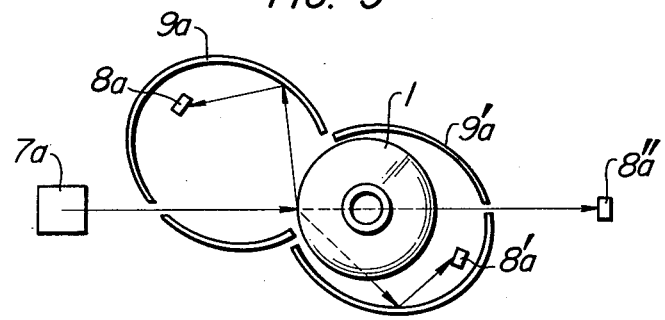

Referring now to FIG. 5 showing a plan view of still another embodiment of the invention, the elliptic cylinder 9a' of the second embodiment is displaced such that one of its foci occupies the same position as one of the foci of the elliptic cylinder 9a.

In the foregoing embodiments, the photoelectric conversion light receiving element or elements are constituted by one or a plurality of photoelectric elements such as solar cell, photodiode, phototransistor and the like, whose output are connected to an amplifier neglected in the drawings. These element or elements produces otput signals, upon receipt of irregularly reflected light, so that the presence of defects such as flaw, contamination and the like in the body of the bottle can be detected through suitably amplifying the output signal from the light receiving element or elements.

Needless to say, the laser light source as used in the foregoing embodiment can be substituted by other light source means such as a tungsten lamp, halogen lamp, mercury lamp, luminescent diode or other known light source, provided that the light emitted from these light source means is suitably focussed on a point.

It will be seen from the foregoing description of the preferred embodiments that the present invention greatly contributes to the field of bottle inspection, through providing an apparatus highly effective in automatically inspecting the bottles for detecting defects such as flaw, contamination and the like.

Conventionally, the inspection of newly produced bottles, as well as that of collected used bottles entirely owed to inefficient observation by naked eyes, at a cost of considerable amount of labor.

It is remarkable that such an inefficient and troublesome inspection work can be eliminated by the use of the bottle inspection apparatus in accordance with the invention.

What is claimed is:

1. An apparatus for inspecting bottles having an elliptic light converging means characterized by comprising: means for applying a beam of light to a rotating bottle to be inspected, said beam of light being applied in parallel with the axis of rotation of said bottle; reflecting means having a reflective surface for reflecting and converging the light reflected by said bottle irregularly due to the presence of defect in said bottle, said reflecting means including at least one open-sided elliptic cylinder having a first and a second foci disposed such that the portion of said bottle to which said beam of light is applied is positioned on the first focus while the light reflected by said reflective surface is converged on the second focus; and at least one light receiving element disposed at said second focus.

2. An apparatus for inspecting bottles having an elliptic light converging means, said apparatus being adapted to detect any defect such as flaw or contamination in said bottle through receiving irregularly reflected light due to the presence of said defect, upon applying light from a light source to said bottle under rotation, characterized by comprising an open-sided elliptic cylinder disposed in the vicinity of said bottle, said elliptic cylinder having a reflective inner surface and a slit through which said light is applied to said bottle, said elliptic cylinder being so arranged that the portion of said bottle to which said light is applied is located on one of the two foci of said elliptic cylinder; at least one light receiving element disposed on the other focus of said elliptic cylinder and adapted to receive a fraction of light irregularly reflected by said bottle; and a multi-surface rotary mirror adapted to reflect the light emitted from said light source in such a manner that the light reflected by said multi-surface rotary mirror scan said bottle along a line in parallel with the axis of said bottle.

3. An apparatus for inspecting bottles having an elliptic light converging means, said apparatus being adapted to detect any defect such as flaw or contamination in the bottle through receiving light irregularly reflected by said bottle due to the presence of said defect, upon applying light from a light source to said bottle under rotation, characterized by comprising an open-sided elliptic cylinder disposed in the vicinity of said bottle such that the portion of said bottle to which said light is applied is located on one of the foci of said elliptic cylinder, said elliptic cylinder having a reflective inner surface and a slit through which said light is applied to said bottle; at least one light receiving element disposed at the other focus of said elliptic cylinder and adapted to receive a fraction of light irregularly reflected by said bottle; at least one light receiving element disposed outside of said elliptic cylinder and adapted to receive a fraction of light passed through said bottle; and a multi-surface rotary mirror adapted to reflect the light from said light source in such a manner that the light reflected by said multi-surface rotary mirror scan said bottle along a line in parallel with the axis of said bottle.

4. An apparatus for inspecting bottles having an elliptic light converging means, said apparatus being adapted to detect defect such as flaw or contamination in said bottle, through receiving light irregularly reflected by said bottle due to the presence of said defect, upon applying light from a light source to said bottle under rotation, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where the light having passed through said bottle leaves the same is located on one of the two foci of said second elliptic cylinder, said second elliptic cylinder having a reflective inner surface and a slit through which the light having passed through said bottle is made to pass; at least one light receiving element disposed at each of the other foci of said first and second elliptic cylinders and adapted to receive irregularly reflected fractions of light; and a multi-surface rotary mirror adapted to reflect the light emitted from said light source in such a manner that the light reflected by said multi-surface rotary mirror scans said bottle along a line in parallel with the axis of said bottle.

5. An apparatus for inspecting bottles having an elliptic light converging means, said apparatus being adapted to detect defect such as flaw or contamination in said bottle, through receiving light irregularly reflected due to the presence of said defect, upon applying light from a light source to said bottle under rotation, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where said light is applied is located on one of the two foci of said second elliptic cylinder, said second elliptic cylinder having a reflective inner surface and a slit through which the fraction of light having passed through said bottle is made to pass; at least one light receiving element disposed at each of the other foci of said first and second elliptic cylinders and adapted to receive the irregularly reflected fractions of light; and a multi-surface rotary mirror adapted to reflect the light emitted from said light source in such a manner that the light reflected by said multi-surface rotary mirror scans said bottle along a line in parallel with the axis of said bottle.

6. An apparatus for inspecting bottles having an elliptic light converging means, said apparatus being adapted to detect defect such as flaw or contamination in said bottle, through receiving light irregularly reflected by said bottle due to the presence of said defect, upon applying light from a light source to said bottle under rotation, characterized by comprising an open-sided elliptic cylinder disposed at the light incident side of said bottle such that the portion of said bottle where said light is applied is located on one of the two foci of said elliptic cylinder, said elliptic cylinder having a reflective inner surface and a slit through which said light is applied to said bottle; at least one light receiving element disposed at the other focus of said elliptic cylinder and adapted to receive irregularly reflected fraction of light; means for changing said light from said light source into a flattened beam of light parallel to the axis of said bottle; and a mirror adapted to reflect and direct said flattened beam of light to said bottle; wherein said elliptic cylinder, light receiving element and said mirror constitutes a unitary block adapted to be moved in the axial direction of said bottle during the inspection.

7. An apparatus as claimed in claim 6, comprising a plurality of blocks each of which having an open-sided elliptic cylinder, light receiving element and a mirror, wherein said mirrors other than the one remotest from said light source are half mirrors.

8. An apparatus for inspecting bottles having an elliptic light converging means, said apparatus being adapted to detect defect such as flaw or contamination in said bottle, through receiving irregularly reflected fraction of light due to the presence of said defect, upon applying light from a light source to said bottle under rotation, characterized by comprising an open-sided elliptic cylinder disposed at the light incident side of said bottle, said elliptic cylinder having a reflective inner surface and a slit through which said light is applied to said bottle, said elliptic cylinder being so located that the portion of said bottle where said light is applied is positioned on one of the two foci of said elliptic cylinder; at least one light receiving element disposed at the other focus of said elliptic cylinder and adapted to receive irregularly reflected fraction of light, at least one another light receiving element adapted to receive the fraction of light passed through said bottle, said another light receiving element being disposed outside of said elliptic cylinder; means for changing said light emitted from said light source into a flattened beam of light parallel to the axis of said bottle, and a mirror adapted to reflect and direct the flattened beam of light to said bottle; wherein said elliptic cylinder, said light receiving element and said mirror forming a unitary block which is moved in the axial direction of said bottle during the inspection.

9. An apparatus as claimed in claim 8, characterized by comprising a plurality of blocks disposed one above the other, each of said block having an open-sided elliptic cylinder, light receiving element and a cylinder, wherein mirrors other than the one remotest from said light source are half mirrors.

10. An apparatus for inspecting bottles having an elliptic light converging means, said apparatus being adapted to detect defect such as flaw or contamination in said bottle, through receiving fraction of light reflected by said bottle irregularly due to the presence of said defect, upon applying light from a light source to said bottle under rotation, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where the fraction of light having passed through said bottle leaves the same is located at one of the two foci of said second elliptic cylinder, said second elliptic cylinder having a reflective inner surface and a slit through which said fraction of light having left said bottle is made to pass; at least one light receiving element disposed at each of the other foci of said first and second elliptic cylinders and adapted to receive irregularly reflected fractions of light; means for changing the light emitted from said light source into a flattened beam of light parallel to the axis of said bottle; and a mirror adapted to reflect and direct said flattened beam of light to said bottle, wherein said elliptic cylinders, said light receiving elements and said mirror constitute a unitary block which is moved in the axial direction of said bottle during the inspection.

11. An apparatus for inspecting bottles having an elliptic light converging means, said apparatus being adapted to detect defect such as flaw or contamination in said bottle, through receiving light irregularly reflected due to the presence of said defect, upon applying light from a light source to said bottle under rotation, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where said light is applied is located on one of the two foci of said second elliptic cylinder, said second elliptic cylinder having a reflective inner surface and a slit through which the fraction of light having passed through said bottle is made to pass; at least one light receiving element disposed at each of the other foci of said first and second elliptic cylinders and adapted to receive the irregularly reflected fractions of light; means for changing said light from said light source into a flattened beam of light parallel to the axis of said bottle; and a mirror adapted to reflect and direct said flattened beam of light to said bottle; wherein said elliptic cylinder, light receiving element and said mirror constitutes a unitary block adapted to be moved in the axial direction of said bottle during the inspection.

12. An apparatus as claimed in claim 11, comprising a plurality of blocks each of which having an open-sided elliptic cylinder, light receiving element and a mirror, wherein said mirrors other than the one remotest from said light source are half mirrors.

13. An apparatus as claimed in claim 10, characterized by comprising a plurality of blocks disposed one above another, each of said blocks including open-sided elliptic cylinders, light receiving elements and a mirror, wherein the mirrors other than the one remotest from said light source are half mirrors.

14. An apparatus for inspecting bottles having an elliptic light converging means, said apparatus being adapted to detect defect such as flaw or contamination in said bottle through receiving fraction of light irregularly reflected by said bottle due to the presence of said defect, upon applying light from a light source to said bottle under rotation, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder, such that the portion of said bottle where the fraction of light having passed through said bottle leaves the same is located at one of the two foci of said second elliptic cylinder, said second elliptic cylinder having a reflective inner surface and a slit through which the fraction of light leaving said bottle is made to pass; at least one light receiving element disposed at each of the other foci of said first and second elliptic cylinders and adapted to receive the irregularly reflected fraction of light; another light receiving element disposed outside of said elliptic cylinders and adapted to receive said fraction of light having passed through said bottle; means for changing said light emitted from said light source to a flattened beam of light parallel to the axis of said bottle; and a mirror adapted to reflect and direct said flattened beam of light to said bottle, wherein said elliptic cylinders, said light receiving elements and said mirror constitute a unitary block adapted to be moved in the axial direction of the bottle during the inspection.

15. An apparatus as claimed in claim 14, characterized by comprising a plurality of blocks disposed one above another, each of said blocks including open-sided elliptic cylinders, light receiving elements and mirrors, wherein the mirrors other than the one remotest from said light source are half mirrors.

16. An apparatus for inspecting bottles having an elliptic light converging means, said apparatus being adapted to detect defect such as flaw or contamination in said bottle through receiving fraction of light reflected by said bottle irregularly due to the presence of said defect, upon applying light from a light source to said bottle while the latter is rotating and moving up and down in the axial direction, characterized by comprising an open-sided elliptic cylinder disposed at the light incident side of said bottle such that the portion of said bottle where said light is applied is located at one of the two foci of said elliptic cylinder, said elliptic cylinder having a reflective inner surface and a slit through which said light is applied to said bottle; at least one light receiving element disposed at the other focus of said elliptic cylinder and adapted to receive irregularly reflected fraction of light; means for changing said light emitted from said light source into a flattened beam of light parallel to the axis of said bottle; and a mirror adapted to reflect and direct said flattened beam of light ot said bottle.

17. An apparatus as claimed in claim 16, characterized by comprising a plurality of blocks arranged one above another, each of said blocks including said open-sided elliptic cylinder, light receiving element and said mirror, wherein the mirrors other than the one remotest from said light source are half mirrors.

18. An apparatus for inspecting bottles having an elliptic light converging means, said apparatus being adapted to detect defect such as flaw or contamination in said bottle through receiving fraction of light reflected by said bottle irregularly due to the presence of said defect, upon applying light from a light source to said bottle while the latter is rotating and moving up and down in the axial direction; characterized by comprising an open-sided elliptic cylinder disposed at the light incident side of said bottle such that the portion of said bottle where said light is applied is located on one of the two foci of said elliptic cylinder, said elliptic cylinder having a reflective inner surface and a slit through which said light is applied to said bottle; at least one light receiving element disposed at the other focus of said elliptic cylinder and adapted to receive the fraction of light irregularly reflected by said bottle; another light receiving element disposed outside of said elliptic cylinder and adapted to receive the fraction of light having passed through said bottle; means for changing the light from said light source into a flattened beam of light parallel to the axis of said bottle; and a mirror for reflecting and directing said flattened beam of light to said bottle.

19. An apparatus as claimed in claim 18, characterized by comprising a plurality of blocks arranged one above another, each of said blocks having said open-sided elliptic cylinder, light receiving element and mirror, wherein the mirrors other than the one remotest from said light source are half mirrors.

20. An apparatus for inspecting bottles having an elliptic light converging means, said apparatus being adapted to detect defect such as flaw or contamination in said bottle through receiving fraction of light reflected by said bottle irregularly due to the presence of said defect, upon applying light from a light source to said bottle while the latter is rotating and moving up and down in the axial direction, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where the fraction of light having passed through the bottle leaves the same is located on one of the two foci of said second elliptic cylinder, said second elliptic cylinder having a reflective inner surface and a slit through which said fraction of light having left said bottle is made to pass; at least one light receiving element disposed at each of the other foci of said first and second elliptic cylinders and adapted to receive fractions of light irregularly reflected by said bottle; means for changing the light emitted from said light source into a flattened beam of light parallel to the axis of said bottle; and a mirror adapted to reflect and direct said flattened beam of light to said bottle.

21. An apparatus as claimed in claim 20, characterized by comprising a plurality of blocks disposed one above another, each of said blocks having said open-sided elliptic cylinders, light receiving elements and mirror, wherein the mirrors other than the one remotest from said light source are half mirrors.

22. An apparatus for inspecting bottles having an elliptic light converging means, said apparatus being adapted to detect defect such as flaw or contamination in said bottle, through receiving fraction of light reflected by said bottle irregularly due to the presence of said defect, upon applying light from a light source to said bottle while the latter is rotating and moving up and down in the axial direction, characterized by comprising a first open-sided elliptic cylinder disposed at the light incident side of said bottle such that the portion of said bottle where said light is applied is located on one of the two foci of said first elliptic cylinder, said first elliptic cylinder having a reflective inner surface and a slit through which said light is applied to said bottle; a second open-sided elliptic cylinder disposed at opposite side of said bottle to said first elliptic cylinder such that the portion of said bottle where the fraction of light having passed through said bottle leaves the same is located on one of the two foci of said second elliptic cylinder, said second elliptic cylinder having a reflective inner surface and a slit through which said fraction of light having left said bottle is made to pass; at least one light receiving element disposed at each of the other foci of said first and second elliptic cylinders and adapted to receive fractions of light reflected irregularly by said bottle; another light receiving element disposed outside of said elliptic cylinders and adapted to receive said fraction of light having passed through and left said bottle; means for changing the light from said light source into a flattened beam of light parallel to the axis of said bottle; and a mirror adapted to reflect and direct said flattened beam of light to said bottle.

23. An apparatus as claimed in claim 22, characterized by a plurality of blocks disposed one above another each of said blocks having said open-sided elliptic cylinders, light receiving elements and mirror, wherein the mirrors other than the one remotest from said light source are half mirrors.

* * * * *